(12) United States Patent
Su

(10) Patent No.: US 10,316,285 B2
(45) Date of Patent: Jun. 11, 2019

(54) MICROFLUIDIC DEVICE

(71) Applicants: Wen-Hong Su, Kaohsiung (TW); Pei-Chin Chuang, Kaohsiung (TW)

(72) Inventor: Wen-Hong Su, Kaohsiung (TW)

(73) Assignees: Wen-Hong Su, Kaohsiung (TW); Pei-Chin Chuang, Kaohsiung (TW)

( * ) Notice: Subject to any disclaimer, the term of this patent is extended or adjusted under 35 U.S.C. 154(b) by 208 days.

(21) Appl. No.: 15/379,928

(22) Filed: Dec. 15, 2016

(65) Prior Publication Data

US 2018/0031564 A1 Feb. 1, 2018

(30) Foreign Application Priority Data

Jul. 29, 2016 (TW) .............................. 105124078 A

(51) Int. Cl.
 *C12N 5/00* (2006.01)
(52) U.S. Cl.
 CPC .................................. *C12N 5/0018* (2013.01)
(58) Field of Classification Search
 CPC .............................. C12N 5/0018; C12M 23/16
 See application file for complete search history.

(56) References Cited

U.S. PATENT DOCUMENTS

| | | | | |
|---|---|---|---|---|
| 6,653,124 B1* | 11/2003 | Freeman | ............... | B01L 3/5027 |
| | | | | 435/286.5 |
| 2006/0199260 A1* | 9/2006 | Zhang | ................. | B01F 13/0059 |
| | | | | 435/293.1 |
| 2013/0295551 A1* | 11/2013 | Eddington | ........... | A01N 1/0247 |
| | | | | 435/1.2 |

\* cited by examiner

*Primary Examiner* — Paul S Hyun
(74) *Attorney, Agent, or Firm* — Rabin & Berdo, P.C.

(57) ABSTRACT

Provided is a microfluidic device, having at least one fluid compartment, an aerator, at least one connecting tube, and a peristaltic pump. The at least one fluid compartment has a base frame, a culture layer, and a flow layer. The culture layer has a base layer and an intermediate layer, and the intermediate layer has at least one opening formed through the intermediate layer to form at least one culture chamber. The flow layer has a top frame layer, a fluid layer, and a transparent layer. The top frame layer has two channels and a hollow. The fluid layer has at least one fluid chamber which communicates with the at least one culture chamber of the culture layer. The at least one connecting tube connects the two channels of the top frame layer of the fluid compartment, the aerator, and the peristaltic pump.

20 Claims, 18 Drawing Sheets

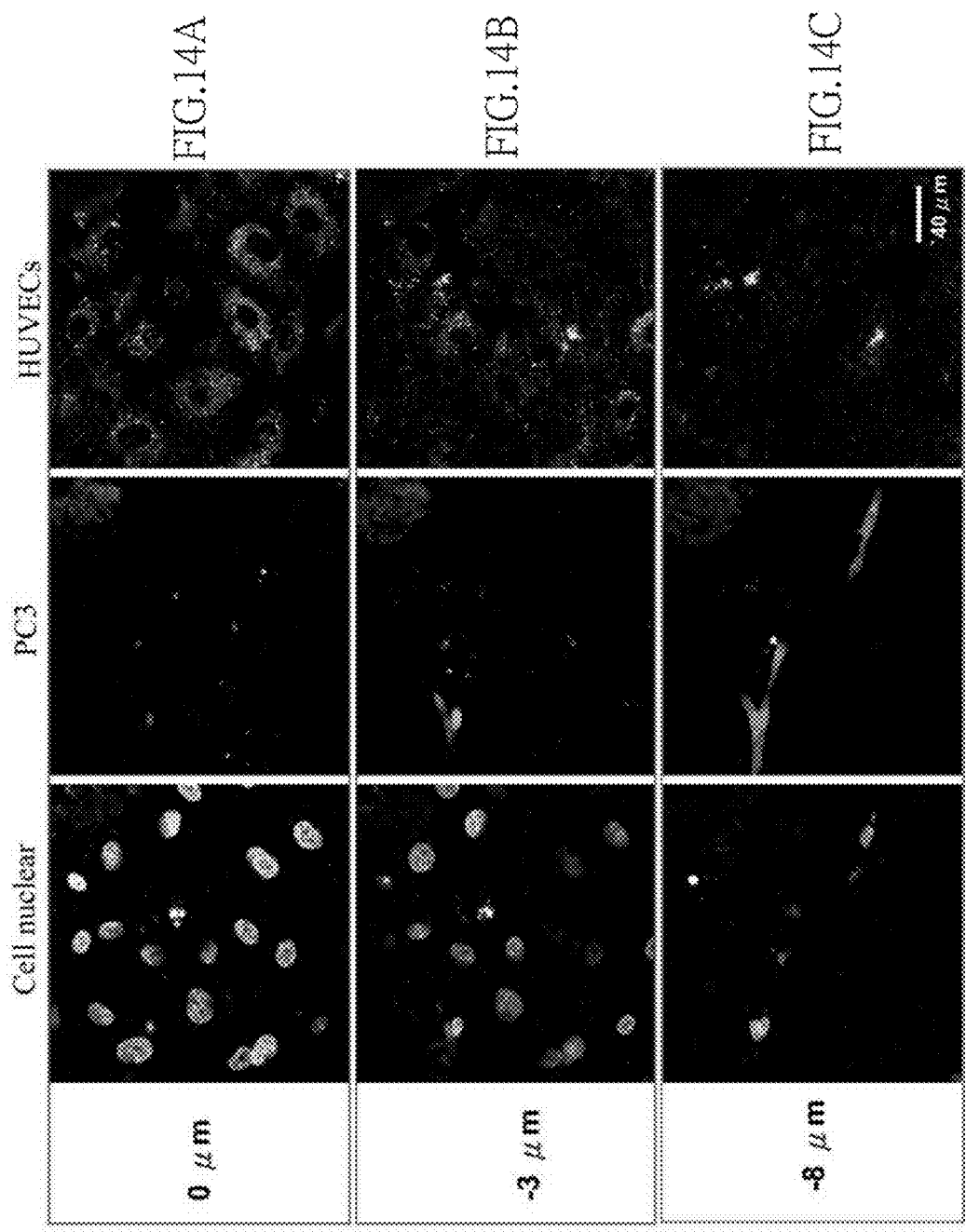

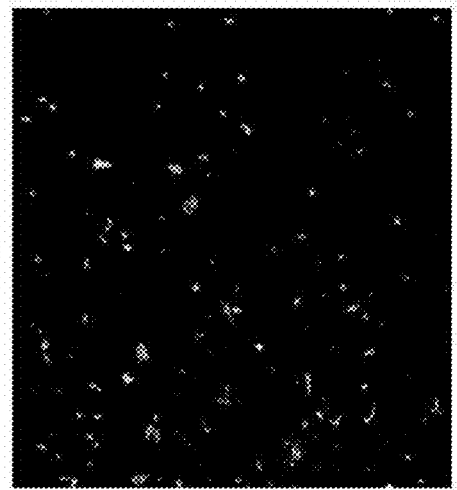
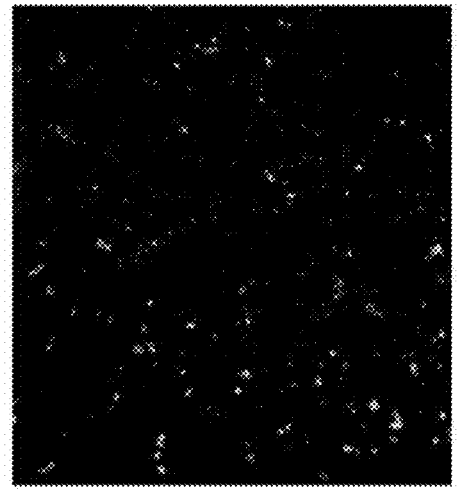
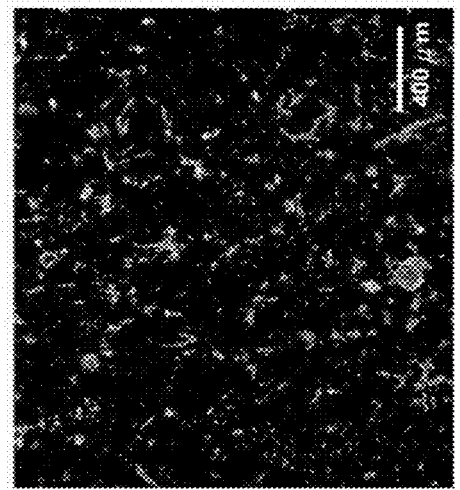
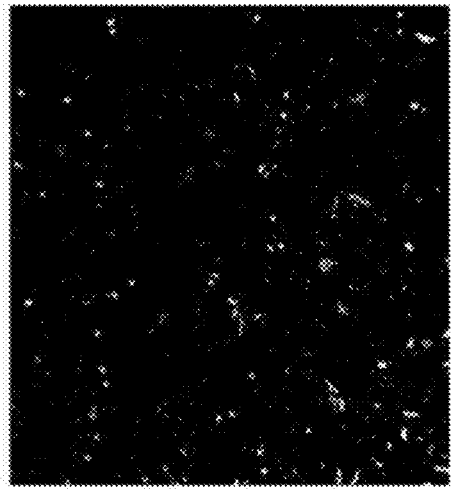

MICROFLUIDIC DEVICE

CROSS REFERENCE TO RELATED APPLICATION

This application claims priority to Taiwan Patent Application Serial No. 105124078, filed on Jul. 29, 2016, the content of which is hereby incorporated by reference in its entirety.

BACKGROUND OF THE INVENTION

1. Field of the Invention

The present invention relates to a microfluidic device, and more particularly to the microfluidic device that can simulate the activity of cells over a long period of time. The present invention further relates to a method for cell culture, cell observation, cell metastasis, cell invasion or cell adhesion of the microfluidic device. The present invention further relates to a method of using the microfluidic device.

2. Background of the Related Art

Metastasis is a complex and important pathogenic mechanism of malignant tumors. Distant metastasis of cancer pathogenesis transfer mechanism is a very complex and important process, but unfortunately, methods and apparatus used to evaluate distal metastasis of cancer cells in vitro are relatively few, and the evaluation method is not comprehensive. Conventional methods for evaluating distant metastasis are as follows: time lapse migration assay, wound healing assay, MMP activity assay, transwell migration assay, transwell invasion assay, cell adhesion assay, flow chamber rolling adhesion assay, anoikis assay, and cell adhesion assay; wherein time lapse migration assay, wound healing assay, MMP activity assay, transwell migration assay, transwell invasion assay are only for evaluating local invasion capability. Anoikis assay can only evaluate cancer survival in the circulation. Flow chamber rolling adhesion assay and cell adhesion assay can only assess arresting capability in the distal end. In the prior art, Transwell® is commonly used to assess transendothelial migration and extravasation (particularly to cancer cells across the endothelial barrier). Moreover, a fluid chamber system also can be used to observe the transfer of leukocyte across the endothelia in the prior art. However, the rate of cancer migration is too slow to evaluate. The foregoing prior arts are not good systems for evaluating distant metastasis, for example, migration, proteinase activity, and anoikis can only evaluate a single distal metastasis.

Although Transwell® can evaluate a variety of distal metastasis, an intermediate porous membrane of Transwell® would seriously interfere with the light penetration, and it is difficult to observe live cancer cells crossing between the endothelial cells and the extracellular matrix in real-time. Besides, Transwell® still cannot simulate blood flow, and the concentration difference of chemoattractant would be reduced due to long experiment period. Conventionally, only liquid chamber or microfluidic device can simulate the blood flow and has good optical quality, but the disadvantage of such apparatus is unable to sustain long-term stability of the concentration gradient of chemoattractant, and therefore such apparatus is only used in the rolling adhesion analysis.

Regarding assessment of distant metastasis for cancer cells, a variety of conventional techniques have to be used for cross-examination, and the process of distant metastasis cannot be observed continually. For instance, cancer metastasis assessment via wound healing analysis or Transwell® is difficult to exclude interference with cell proliferation or survival. Moreover, microenvironments of different organs can also affect the ratio of cancer cells transfer to different organs by distant metastases. For example, prostate cancer prefers to transfer into bone tissues. In other words, different cancers have preferences for transferring to different organs, and there is not any system for evaluation in vitro.

The conventional fluid chamber includes the following two categories: (1) cells and culture medium would flow through the fluid chamber only one time, but remaining cells and culture medium would be discarded. It not only fails to reflect the blood flow in reality, but also consumes a lot of culture medium in experimental period; (2) the culture medium can be used cyclically, but cells would accumulate in the system somewhere because of the structure of the aeration device or liquid circulation. Take ibidi pump system fluid system as an example, cells would accumulate at the bottom side of the syringe, cause cell adhesion or mutual stimulation, and even cause cell aggregation, so as to increase the amount of cells and interfere with results.

In addition, in order to attract cells to cross through endothelial cells and extracellular matrix, porous membrane or gel is used to separate single chemoattractant at different concentrations to form a concentration gradient in the conventional device. However, the concentration gradient of two chemoattractants would tend to balance and cause the difference of concentration gradient to weaken or even disappear. And the way to maintain the chemoattractant concentration gradient over a long period would be reducing the area of membrane or increasing liquid amount across the membrane. However, both of these methods have their limits and might interfere with experiment operation and the results. Moreover, porous membrane will increase the difficulty of monitoring, and the gel itself is also fragile. Continually changing the solution to maintain the concentration gradient will also disturb the experiment such as unadhered cells, which would be washed away, or the pressure difference across the membrane. Most importantly, these devices, which use only one chemoattractant at the same time to attract cells to migrate between epithelium cells and ECM layers, are completely different from physiological conditions. In normal physiological conditions, tissue cell will secret sorts of substances, some of which can attract cell migration and the others can directly affect the endothelial cells to change the characteristics of them and let certain cells migrate into the tissue. Accordingly, not only the academia but the medical field are desperate for an ex-vivo system, which can perform continuous monitoring and also can objectively evaluate the capability of cancer cells migration from vessel to distal organs to perform the study of cancer metastasis and prognosis.

SUMMARY OF THE INVENTION

In view of the lack of the complete and continuous observation system for evaluating cancer cell distant metastasis in vitro, the objective of the present invention is to provide a microfluidic device for complete and continuous observation of the processes of cell metastasis, cell invasion or cell adhesion over a long period.

To achieve the above purpose of the present invention, the present invention provides a microfluidic device, comprising at least one fluid compartment, an aerator, at least one connecting tube, and a peristaltic pump. The at least one fluid compartment comprises a base frame, a flow layer, and a culture layer between the base frame and the flow layer. The base frame has a hole; the culture layer comprises a base layer and an intermediate layer stacked on the base layer, and at least one opening is formed through the intermediate layer to form at least one culture chamber. The flow layer comprises a top frame layer, a fluid layer stacked on the top frame layer, and a transparent layer between the top frame layer and the fluid layer. The top frame layer comprises two channels, and a hollow is formed between the two channels and through the top frame layer. The fluid layer has at least one fluid chamber on one of the sides of the fluid layer, the other side of the fluid layer has an aperture, the aperture is connected to the at least one fluid chamber, the opposite ends of the at least one fluid chamber extend away from each other to form grooves, the grooves are respectively connected to the two channels of the top frame layer, and the at least one fluid chamber communicates with the at least one culture chamber of the culture layer. The at least one connecting tube connects the two channels of the top frame layer of the at least one fluid compartment, the aerator, and the peristaltic pump.

Preferably, each of the two channels of the top frame layer of the at least one fluid compartment is formed by a bore and a pore communicating with each other, the bores are each respectively formed in the opposite sides of the surface of the top frame layer, the surface of the top frame layer is in contact with the fluid layer, and the pores are each respectively formed in the opposite sidewalls of the top frame layer.

Preferably, the contour of the transparent layer of the flow layer is larger than the contour the at least one fluid chamber of the flow layer, and the contour of the transparent layer is corresponding to the contour of the aperture of the at least one fluid chamber of the flow layer, so that the transparent layer is mounted in the aperture.

Preferably, the base frame further comprises multiple magnets which are mounted in the base frame and equidistantly surround the hole of the base frame.

Preferably, the flow layer further comprises multiple magnets which are mounted in the top frame layer and equidistantly surround the at least one fluid chamber and the hollow of the fluid layer.

More preferably, the multiple magnets are made of neodymium.

Preferably, the base frame and the top frame layer of the flow layer are made of a rigid material including, but not limited to, hard plastic, acrylic, epoxy, stainless steel, or aluminum.

Preferably, the material of the intermediate layer of the culture layer and the fluid layer of the flow layer is plastic and elastic, and includes, but is not limited to, silicone, latex, rubber, fluorosillicone (FVMQ), or butadiene rubber (BR).

Preferably, the inner wall of the two channels of the top frame layer can be coated with an antiadhesive, the antiadhesive including, but not limited to, [poly(2-hydroxyethyl methacrylate), poly(HEMA)], silicone, polytetrafluoroethylene (PTFE), or silicone oil.

Preferably, the inner wall of the aerator and the at least one connecting tube can be coated with an antiadhesive, the antiadhesive including, but not limited to, poly(HEMA), silicone, PTFE, or silicone oil.

Preferably, the base layer of the culture layer and the transparent layer of the flow layer are made of a light permeable material including, but not limited to, transparent glass slide.

Preferably, the at least one culture chamber can be filled with a biocompatible material, the biocompatible material including, but not limited to, collagen, gelatin, hyaluronic acid, [poly(lactic-co-glycolic acid), PLGA], Matrigel™, tissue decellularized extracellular matrix, or any combination thereof.

Preferably, the number of the at least one fluid chamber is one and the number of the at least one culture chamber is one.

Preferably, the number of the at least one fluid chamber is one, and the number of the at least one culture chamber is two.

Preferably, the base frame, the culture layer, and the flow layer can be sequentially sandwiched together and tightly connected by multiple magnets, screws, clamp, vacuum suction, adhesive, or any other ways.

In some preferred embodiments, the base frame, the culture layer, and the flow layer are connected by attraction of the multiple magnets, which are respectively in the base frame and the flow layer. In other preferred embodiments, the base frame, the culture layer, and the flow layer can be sequentially sandwiched together by clamp or with adhesive to tightly connect to each other. The person skilled in the art may use any other methods, according to the needs, to connect the base frame, the culture layer, and the flow layer together, so that the methods should not be unduly limited to such specific embodiments.

Preferably, the at least one fluid compartment is more than two fluid compartments.

In another aspect, the present invention also provides a method of the above-mentioned microfluidic device for cell culture, cell observation, cell metastasis, cell invasion or cell adhesion in the meantime.

In still another aspect, the present invention further relates to a method of using the above-mentioned microfluidic device, comprising the following steps: preparing first cells; culturing the first cells in the at least one culture chamber; and monitoring the first cells in the at least one culture chamber from the hole of the base frame via the base layer of the culture layer by microscope, or from the hollow of the flow layer via the transparent layer by microscope. Preferably, the method of the step of preparing first cells further includes mixing the first cells with a biocompatible material.

Preferably, the method further includes a step of adding a drug or second cells after the step of culturing the first cells in the at least one culture chamber.

The at least one fluid compartment of the microfluidic device of the present invention can provide a 3D cell culture environment and can entirely monitor the cell migration, cell invasion, or cell adhesion by light microscope or fluorescent microscope in a long term (more than 24 hours). In addition, the at least one culture chamber of the microfluidic device of the present invention can perform various tests at the same time to save time, labor, and consumable costs, and especially reducing the consumption of the cells that are rare (e.g. circulating tumor cells, CTCs). Moreover, cells can be recycled in the microfluidic device of the present invention to physiologically simulate the process of cancer cells distant metastasis. Furthermore, the base frame, the culture layer, and the flow layer not only can be detachably connected to each other to perform the tests including cell culture, pharmaceutical administration, and cell immunostaining conveniently during the microfluidic experiment, but also can remove the tissue or cells from the at least one culture chamber and keep on cell culturing.

Other objectives, advantages and novel features of the invention will become more apparent from the following detailed description when taken in conjunction with the accompanying drawings.

BRIEF DESCRIPTION OF THE DRAWINGS

FIGS. 14A-14C are confocal microscopy images with 600× magnification of the first preferred embodiment of the microfluidic device of the present invention, wherein the blue florescent indicates the positions of cell nuclear by DAPI staining (left columns), the green florescent displays the PC3 prostate cancer cells (middle columns), and the red florescent displays the human umbilical vein endothelial cells (right columns); the depth in FIG. 14A is a base line (0 μm); the depth in FIG. 14B is 3 μm below the depth in FIG. 14A (−3 μm); and the depth in FIG. 14C is 8 μm below the depth in FIG. 14A (−8 μm).

FIGS. 14A to 14C show that the position of the PC3 prostate cancer cells is under the human umbilical vein endothelial cells;

FIG. 15A is an enlarged image with 50× magnification of the control group of the first preferred embodiment of the microfluidic device of the present invention, wherein the green florescent displays the LNCaP prostate cancer cells;

FIG. 15B is an enlarged image with 50× magnification of the control group of the first preferred embodiment of the microfluidic device of the present invention, wherein the green florescent displays the PC3 prostate cancer cells;

FIG. 15C is an enlarged image with 50× magnification of the 3D cultured group of the first preferred embodiment of the microfluidic device of the present invention, wherein the green florescent displays the LNCaP prostate cancer cells;

FIG. 15D is an enlarged image with 50× magnification of the 3D cultured group of the first preferred embodiment of the microfluidic device of the present invention, wherein the green florescent displays the PC3 prostate cancer cells.

DETAILED DESCRIPTION OF THE INVENTION

Figure 1A:
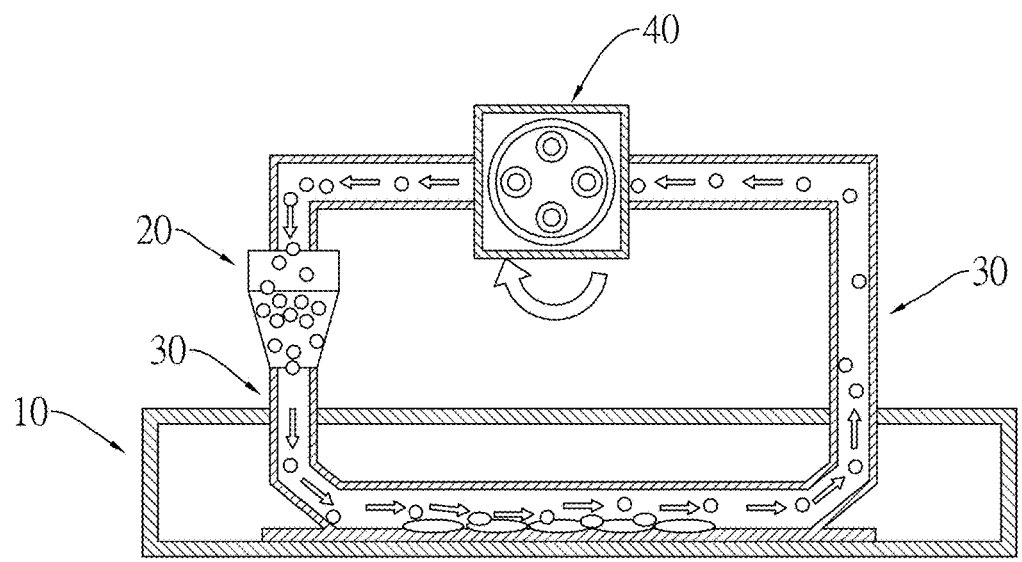
FIG. 1A is a perspective side view of a microfluidic device of the present invention.
Figure 1B:
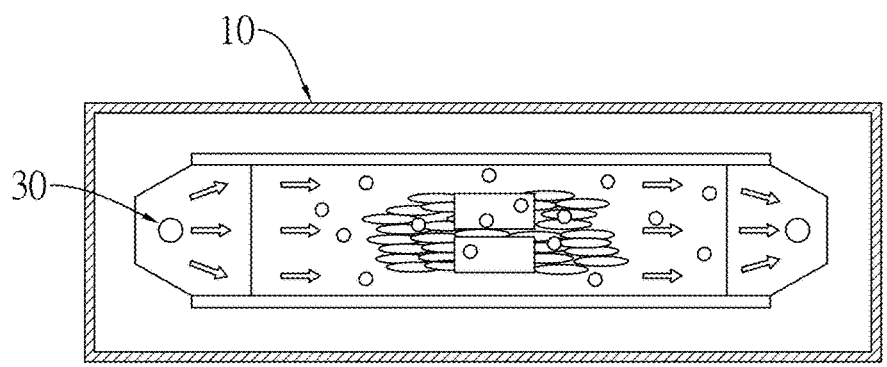
FIG. 1B is a top view of the microfluidic chamber of the present invention.

As shown in FIGS. 1A and 1B, the present invention provides a microfluidic device, comprising a fluid compartment 10, an aerator 20, at least one connecting tube 30, and a peristaltic pump 40.

Figure 2:
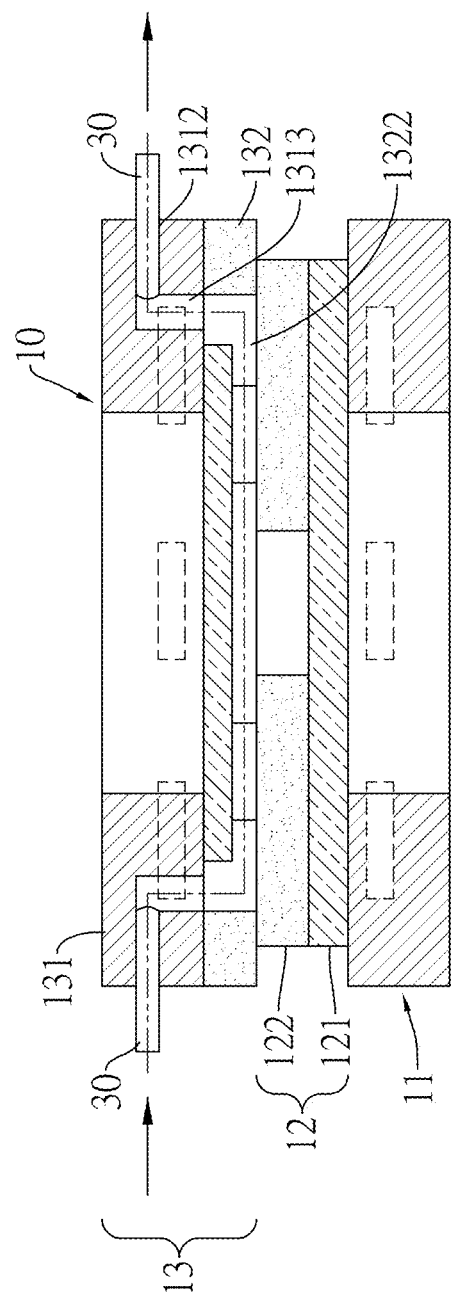
FIG. 2 is a cross-sectional view of the fluid compartment and the connecting tube of the microfluidic device of the present invention.

As shown in FIG. 2, the fluid compartment 10 comprises a base frame 11, a culture layer 12, and a flow layer 13. The culture layer 12 is between the base frame 11 and the flow layer 13, and both of the base frame 11 and the flow layer 13 are detachably connected to the culture layer 12.

Figure 3A:
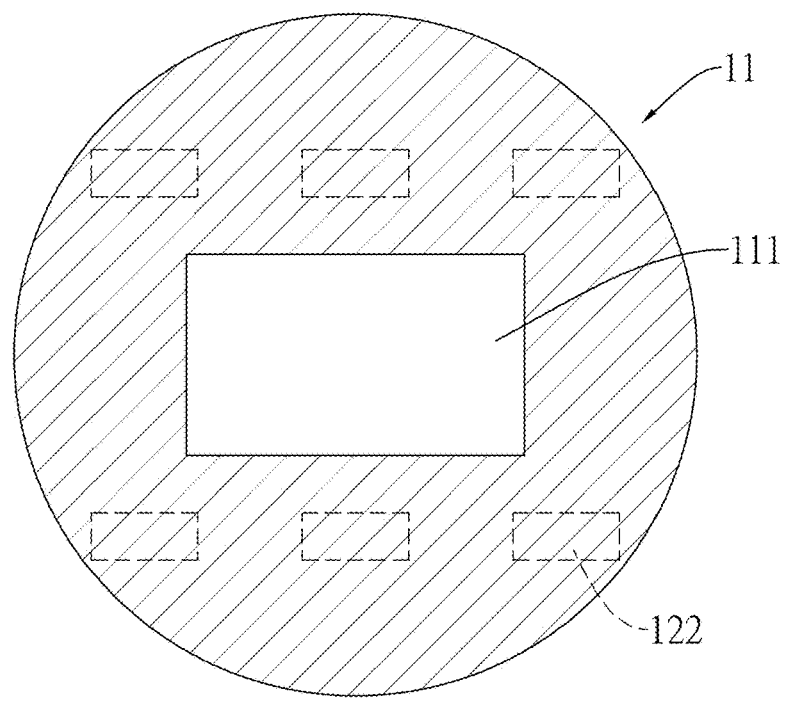
FIG. 3A is a top view of the base frame of the microfluidic device of the present invention.
Figure 3B:
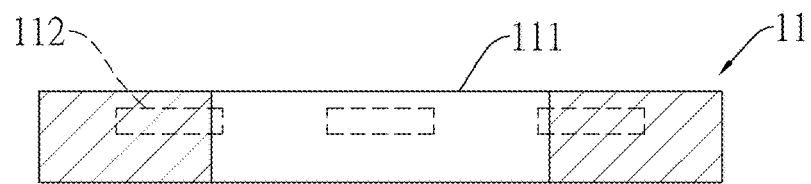
FIG. 3B is a cross-sectional view of the base frame of the microfluidic device of the present invention.

As shown in FIGS. 3A and 3B, the base frame 11 has a hole 111 formed through the base frame 11 for microscope observation. In one preferred embodiment, the base frame 11 is made of a rigid materials such as hard plastic, acrylic, epoxy, stainless steel, or aluminum. In another preferred embodiment, the base frame 11 further comprises multiple magnets 112, and the multiple magnets 112 are mounted in the base frame 11 and equidistantly surround the hole 111 of the base frame 11. The multiple magnets 112 are made of neodymium.

Figure 4A:
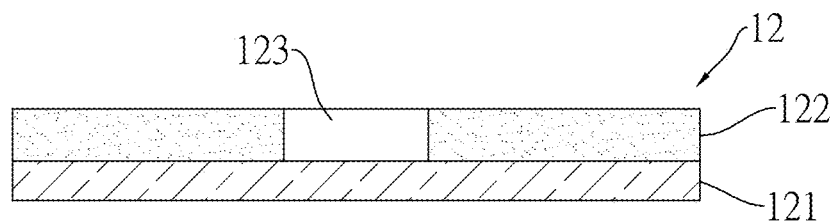
FIG. 4A is a cross-sectional view of the culture layer of the microfluidic device of the present invention.
Figure 4B:
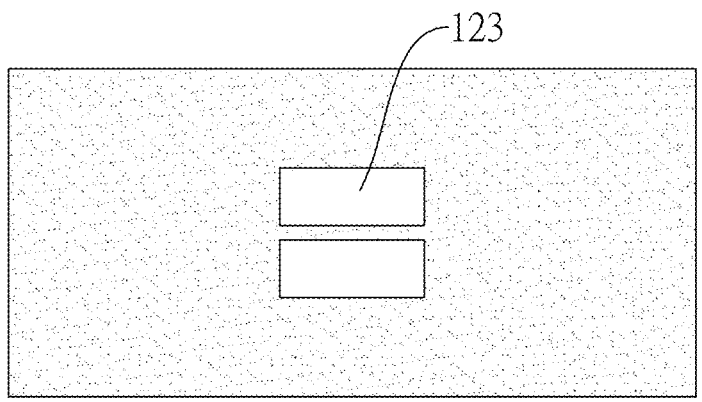
FIG. 4B is a top view of the culture layer of the microfluidic device of the present invention.

As shown in FIGS. 4A and 4B, the culture layer 12 comprises a base layer 121 and an intermediate layer 122. The intermediate layer 122 is stacked on the base layer 121 and is made of plastic material such as silicone. The base layer 121 is made of light-permeable material such as transparent glass slide. The intermediate layer 122 has at least one opening formed through the intermediate layer 122 to form at least one culture chamber 123 of the culture layer 12. In a preferred embodiment, the number of at least one culture chamber 123 is one, two (with reference to FIG. 4B), or five. Each of the at least one culture chamber 123 can be further filled with a biocompatible material for cells growth in the biocompatible material or growth on the surface. The kind of a biocompatible material includes collagen, gelatin, hyaluronic acid, [poly (lactic-co-glycolic acid), PLGA], Matrigel™, tissue decellularized extracellular matrix, and the like for 3D tissue culture. In other embodiments, the biocompatible material could be added with different cancer cells, cancer tissues, cell lines, single type of tissue cells, tissue cells, a cluster of tissues, tissue slices, sustained-release granules, nanoparticles, sustained-release gel, and any substance known in the art suitable for a biocompatible material. The biocompatible material in each of the culture chambers 123 may curd for tissue cells, stem cells or cell line culture to grow on the surface of a biocompatible material.

Figure 5A:
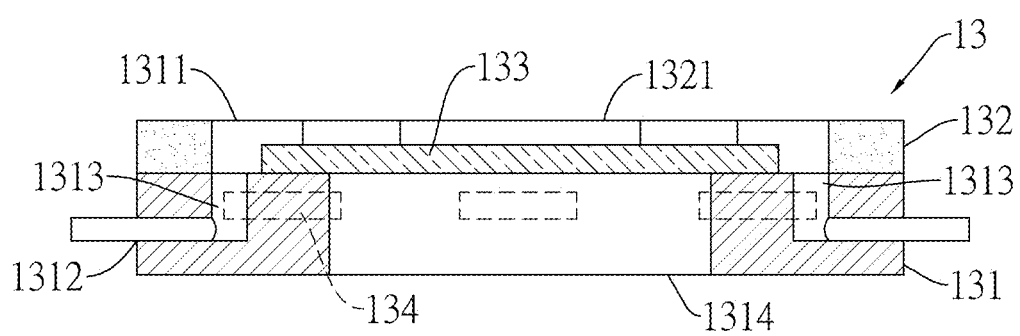
FIG. 5A is a cross-sectional view of the flow layer of the microfluidic device of the present invention.
Figure 5B:
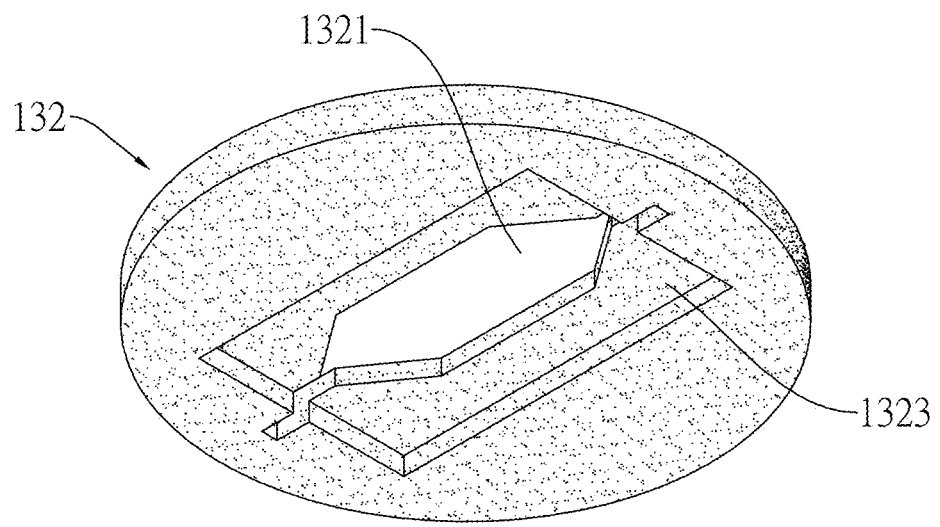
FIG. 5B is a perspective side view of the fluid layer of the flow layer of the microfluidic device of the present invention.
Figure 5C:
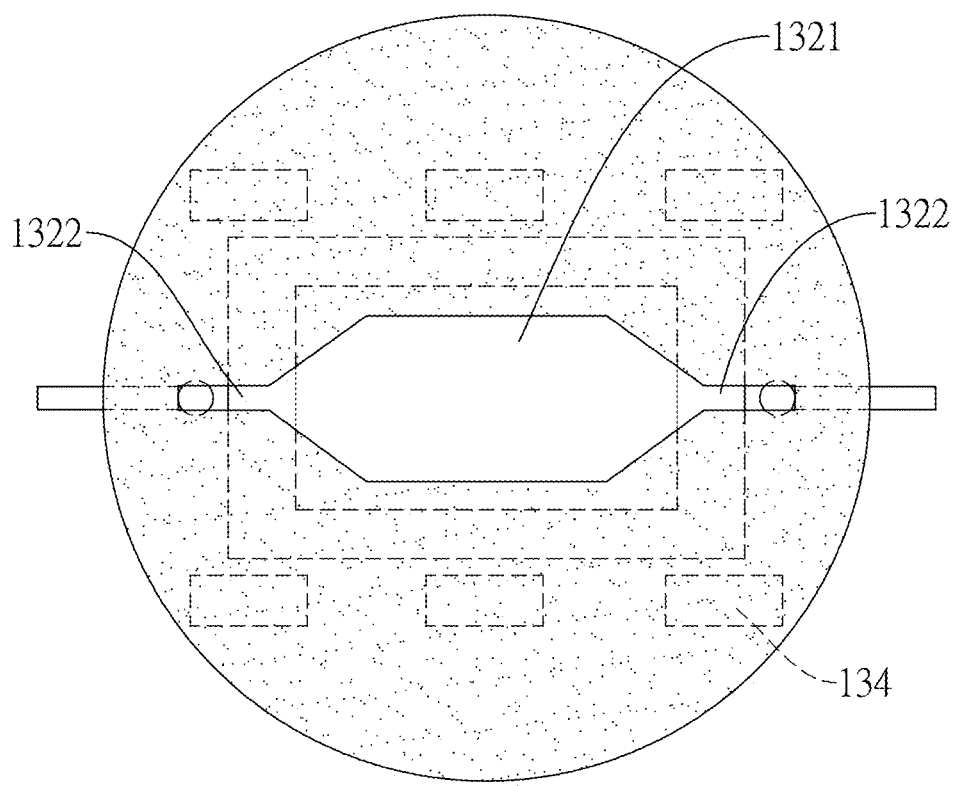
FIG. 5C is a top view of the flow layer of the microfluidic device of the present invention.
Figure 5D:
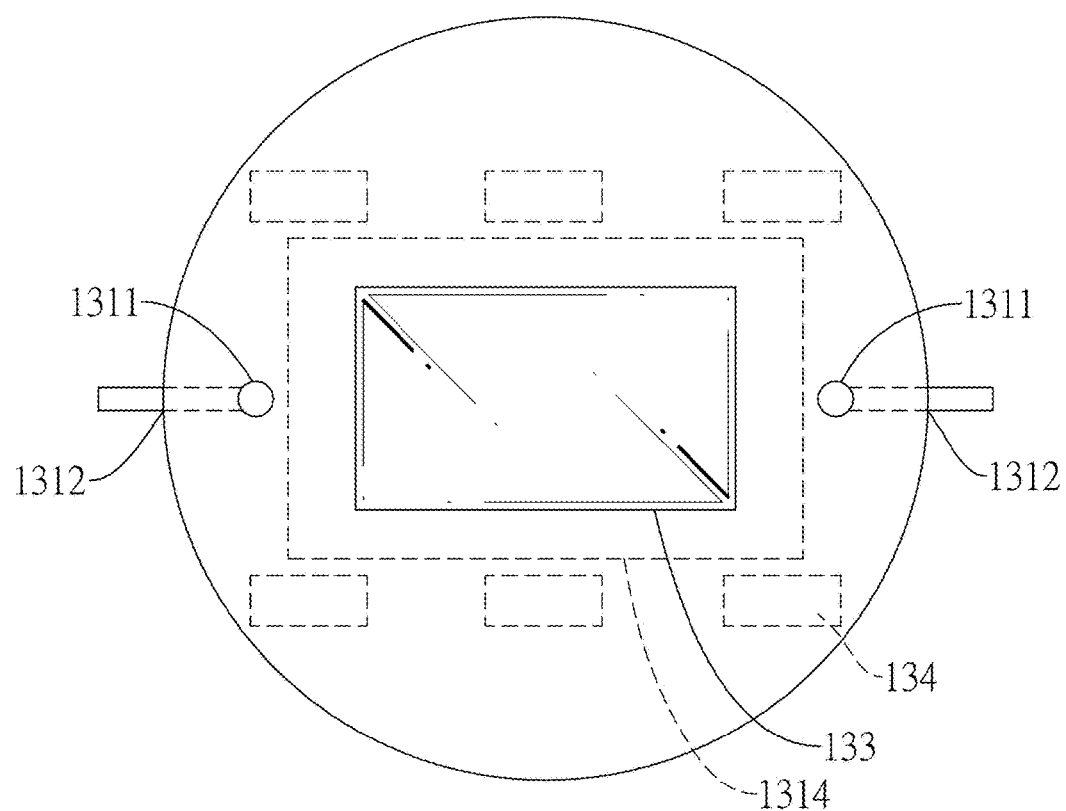
FIG. 5D is a bottom view of the flow layer of the microfluidic device of the present invention.
Figure 6:
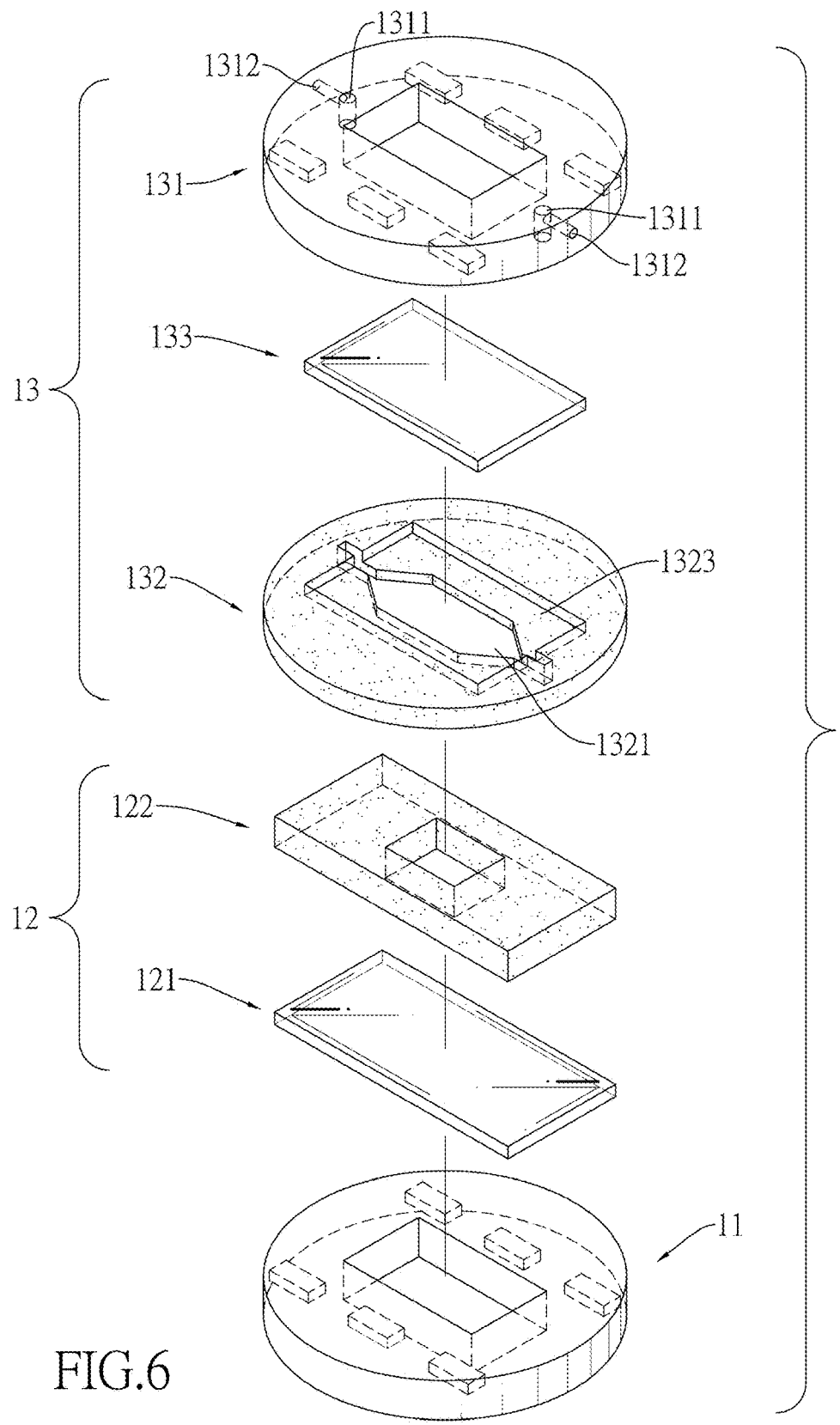
FIG. 6 is an exploded view of the base frame, the culture layer, and the flow layer of the microfluidic device of the present invention.

As shown in FIGS. 5A to 6, the flow layer 13 comprises a top frame layer 131, a fluid layer 132, and a transparent layer 133. Two bores 1311 are each respectively formed at two opposite ends near the edge of the surface of top frame layer 131, two pores 1312 are each respectively formed in the opposite sidewalls of the top frame layer 131, and the bores 1311 are each connected to and communicate with a respective one of the pores 1312 to form two channels 1313. A hollow 1314 is formed through the middle of the top frame layer 131 and between the two channels 1313. The fluid layer 132 is stacked on the top frame layer 131 and at least one fluid chamber 1321 is formed at one of the sides of the fluid layer 132 formed in the at least one fluid chamber 1321. The opposite ends of the at least one fluid chamber 1321 extend away from each other to form two grooves 1322, and the two grooves 1322 each communicate with a respective one of the two channels 1313. The at least one fluid chamber 1321 communicates with each of the culture chambers 123 of the culture layer 12. An aperture 1323 is formed in the other side of the fluid layer 132 and is connected to the at least one fluid chamber 1321. The contour of the transparent layer 133 is larger than the contour of the at least one fluid chamber 1321, and the contour of the transparent layer 13 is equal to the contour of the aperture 1323, so that the transparent layer 133 can be mounted in the aperture 1323. In preferred embodiments, the top frame layer 131 may be made of hard plastic, acrylic, epoxy resin, stainless steel, or aluminum. The fluid layer 132 is made of silicone, and the material of the transparent layer 133 is light-permeable material such as transparent glass slide. The inner wall of the two channels 1313 could be coated with an antiadhesive such as [poly(2-hydroxyethyl methacrylate), poly(HEMA)] to prevent cells adhesion or activation. In another preferred embodiment, the flow layer 13 further comprises multiple magnets 134, and the multiple magnets 134 of the flow layer 13 are equidistantly mounted in the top frame layer 131 and surround the at least one fluid chamber 1321 and the aperture 1323 of the fluid layer 132. The multiple magnets 134 of the flow layer 13 are made of neodymium.

Figure 7:
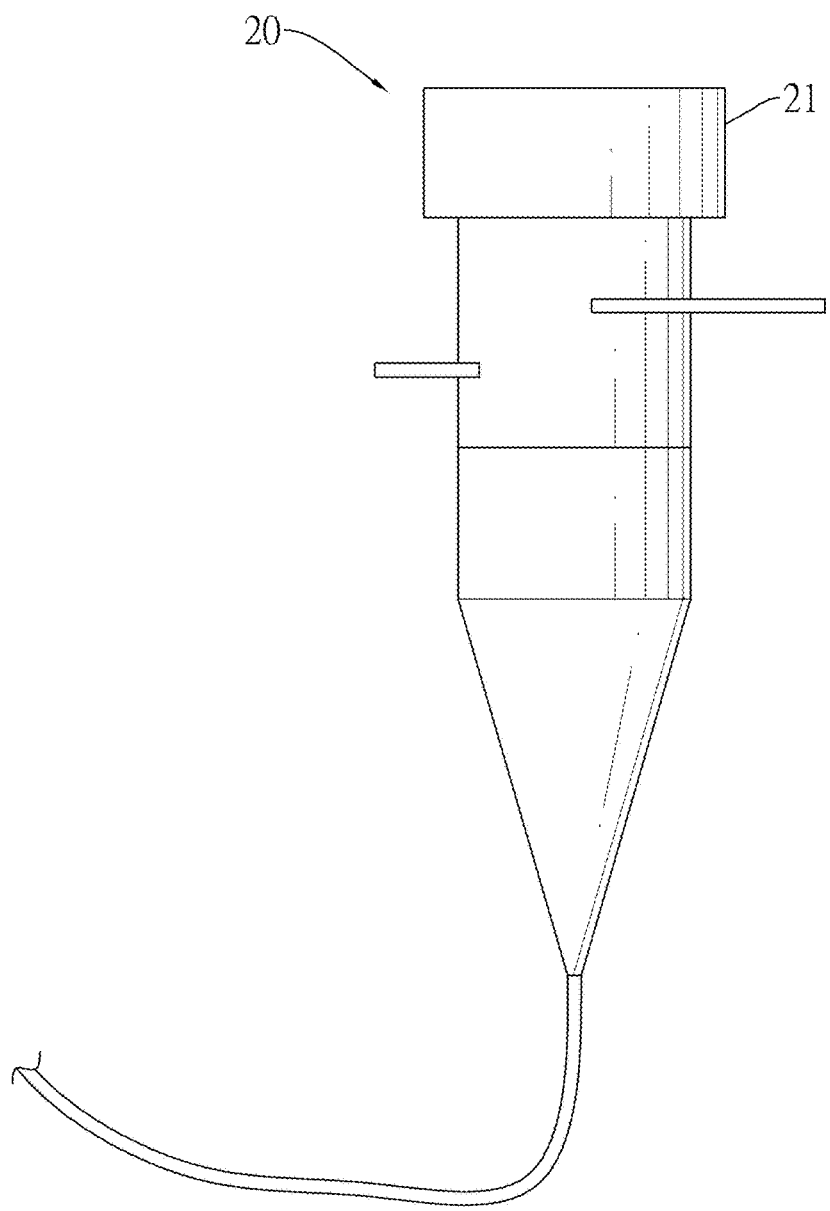
FIG. 7 is a side view of the aerator of the microfluidic device of the present invention.

As shown in FIG. 7, an antibacterial cap 21 that is gas permeable detachably covers the top of the aerator 20. The bottom of the aerator 20 is conical to prevent cell accumulation, and the inner wall of the aerator 20 could be coated with an antiadhesive such as poly(HEMA) to prevent cell adhesion.

As shown in FIGS. 1A to 2, in a preferred embodiment, the at least one connecting tube 30 is two connecting tubes 30. One end of each of the two connecting tubes 30 is inserted to a respective one of the two channels 1313 of the top frame layer 131 of the flow layer 13 of the fluid compartment 10, and the two grooves 1322 of the fluid layer 132 are each connected to a respective one of the two channels 1313 of the top frame layer 131, so that the two connecting tubes 30 are respectively connected to the two channels 1313 of the top frame layer 131 and respectively to the two grooves 1322 of the fluid layer 132. Inner walls of the two connecting tubes 30 could be coated with an antiadhesive, including [poly (2-hydroxyethyl methacrylate), poly(HEMA)] to prevent cells adhesion or activation, wherein the other end of each of the two connecting tubes 30 is connected to the aerator 20 and the peristaltic pump 40.

As shown in FIGS. 1A to 2, one end of the fluid compartment 10 is connected to the aerator 20 by one of the connecting tubes 30 while the aerator 20 is connected to the peristaltic pump 40, the other end of the fluid compartment 10 is connected to the peristaltic pump 40 by the other connecting tube 30. The fluid compartment 10, as stacked from bottom to top, comprises the base frame 11, the base layer 121 of the culture layer 12, the intermediate layer 122 of the culture layer 12, the fluid layer 132 of the flow layer 13, and the top frame layer 131 of the flow layer 13, and the two channels 1313 of the top frame layer 131 are each connected to a respective one of the two grooves 1322 of the fluid layer 132. The base frame 11, the culture layer 12, and the flow layer 13 are connected by attraction of the multiple magnets 112, 134 which are respectively in the base frame 11 and the flow layer 13. In other preferred embodiments, the base frame 11, the culture layer 12, and the flow layer 13 can be sequentially sandwiched together by screws, clamps, vacuum suction, adhesive, or other ways. The two connecting tubes 30 are connected to the two channels 1313 of the top frame layer 131 by being inserted into the two pores 1312, which means that the two connecting tubes 30 are respectively connected to the two grooves 1322 of the fluid layer 132. The end of one of the two connecting tubes 30 that is connected to the fluid compartment 10 is connected to the peristaltic pump 40 by the aerator 20, and the other connecting tube 30, which is also connected to the fluid compartment 10, is connected to the other side of the peristaltic pump 40. Therefore, the culture medium in the aerator 20 can be pumped into the fluid compartment 10 by the peristaltic pump 40 by flowing through one of the two channels 1313 of the top frame layer 131 of the flow layer 13 and one of the grooves 1322 of the fluid layer 132, and then flow out from the fluid compartment 10 via the other groove 1322 and the other channel 1313 into the peristaltic pump 40 again to form a circulation. The microfluidic device of the present invention provides monitoring of the cells in the at least one culture chamber 123 bottom-up via the hole 111 of the base frame 11 and the base layer 121 of the culture layer 12, or top-down via the hollow 1314 of the flow layer 13 and the transparent layer 133 by a microscope, fluorescent microscope, or confocal microscope.

Figure 8:
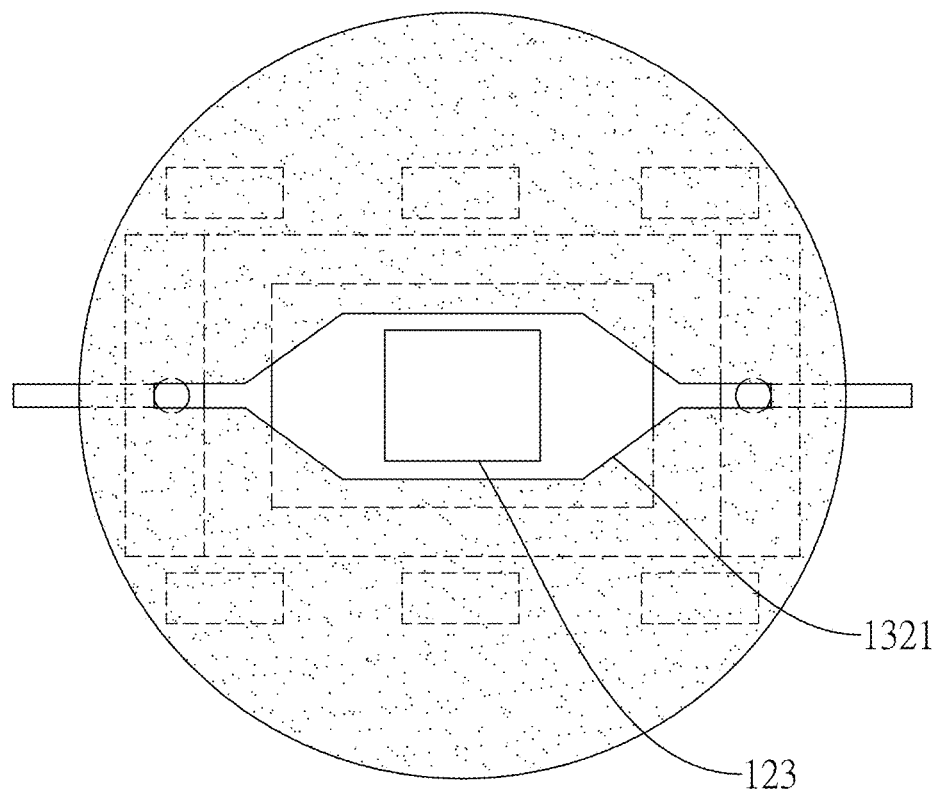
FIG. 8 is a top view of the culture layer with one culture chamber and the flow layer with one fluid chamber of the microfluidic device of the present invention.
Figure 9:
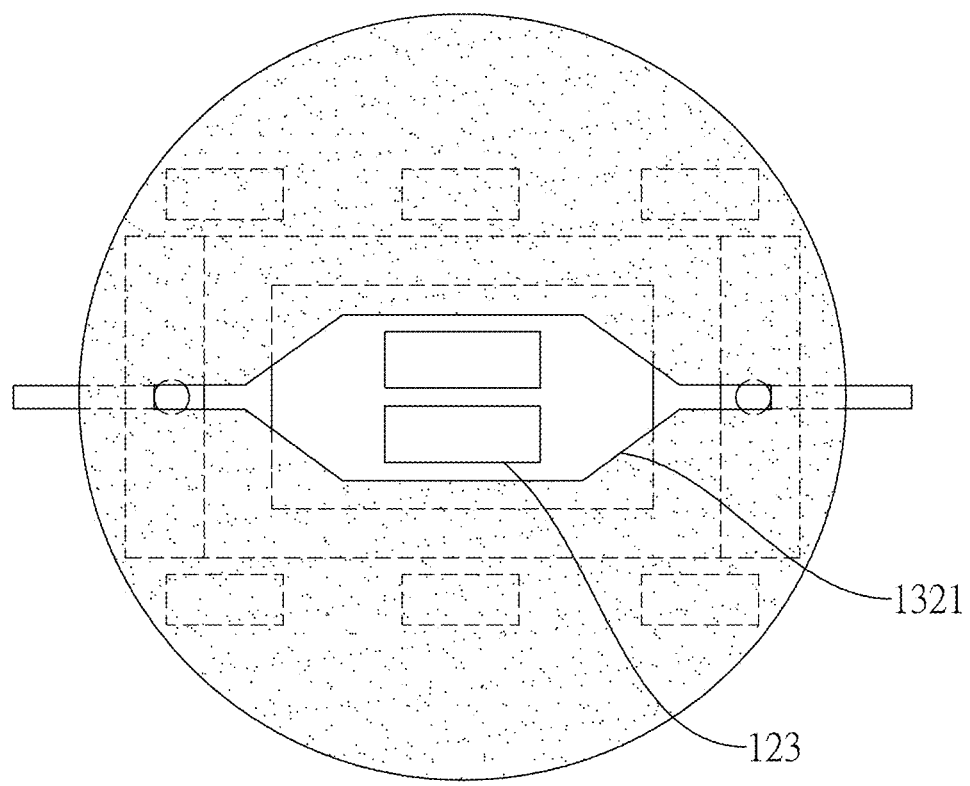
FIG. 9 is a top view of the culture layer with two culture chambers and the flow layer with one fluid chamber of another microfluidic device of the present invention.
Figure 10:
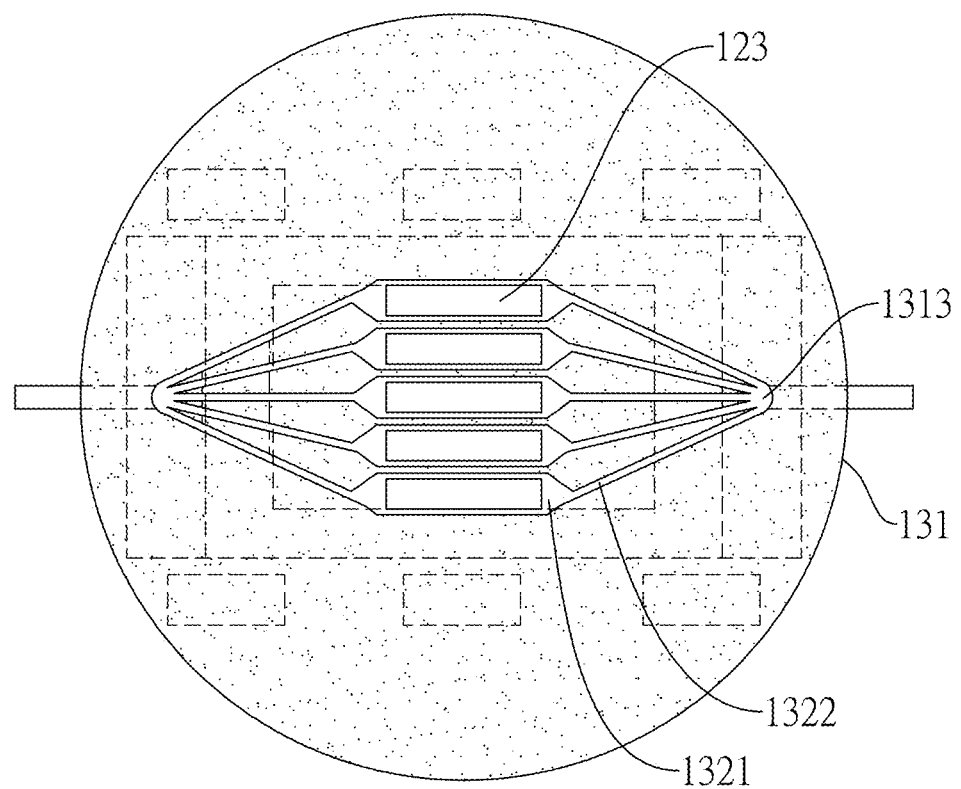
FIG. 10 is a top view of the culture layer with five culture chambers and the flow layer with five fluid chambers of another microfluidic device of the present invention.
Figure 16:
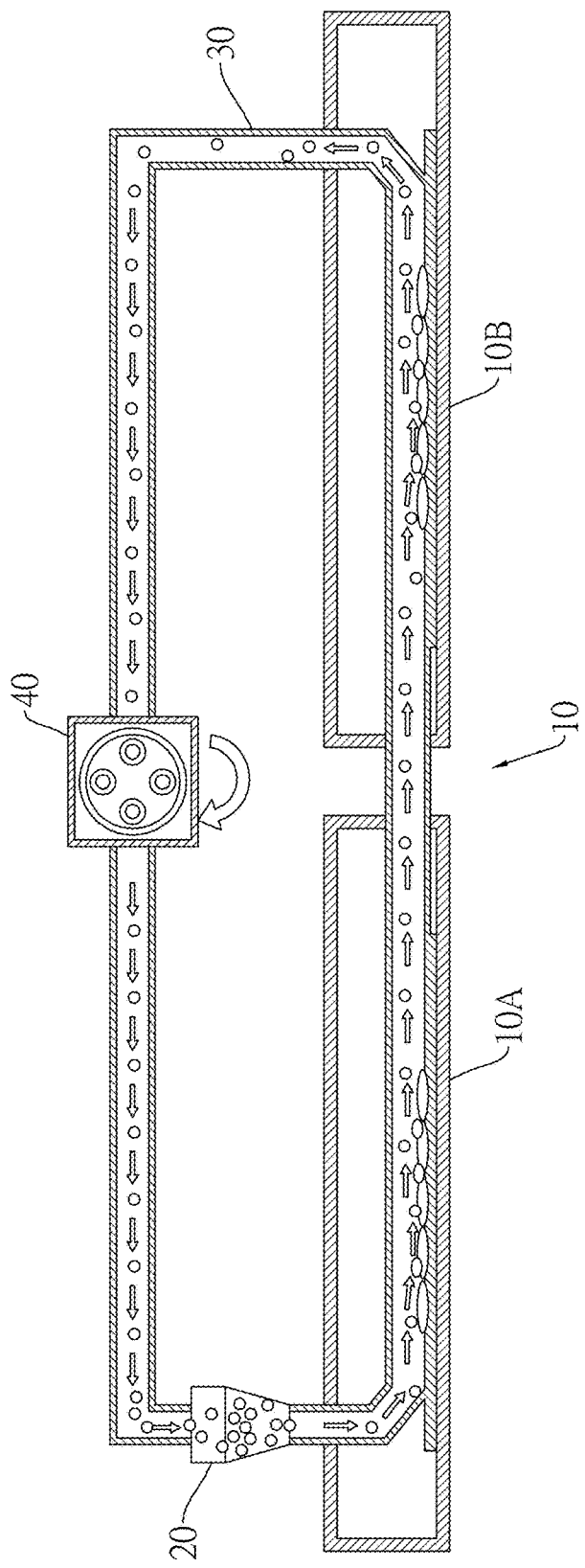
FIG. 16 is a perspective side view of the third preferred embodiment of the microfluidic device of the present invention.

In the first preferred embodiment, as shown in FIG. 8, the number of the at least one fluid chamber 1321 is one, and the number of at least one culture chamber 123 is also one. In the second preferred embodiment, as shown in FIG. 9, the at least one fluid chamber 1321 is one fluid chamber 1321, and the at least one culture chamber 123 is two culture chambers 123. In the third preferred embodiment, as shown in FIG. 10, the at least one fluid chamber 1321 is five fluid chambers 1321 and the at least one culture chamber 123 is one culture chamber 123, and the opposite ends of each of the fluid chambers 1321 extend away from each other to form two grooves 1322, wherein the grooves 1322 gather and connect to the two channels 1313 of the top frame layer 131. Please refer to FIGS. 1A, 2, and 16 for the following examples.

Example 1 Simulation of Organ Microenvironment for Detecting the Invasion Ability of Cancer Cells into Tissue In the first preferred embodiment of the microfluidic device of the present invention, the culture layer 12 has two culture chambers 123 and the fluid layer 132 has one fluid chamber 1321.

Figure 11A:
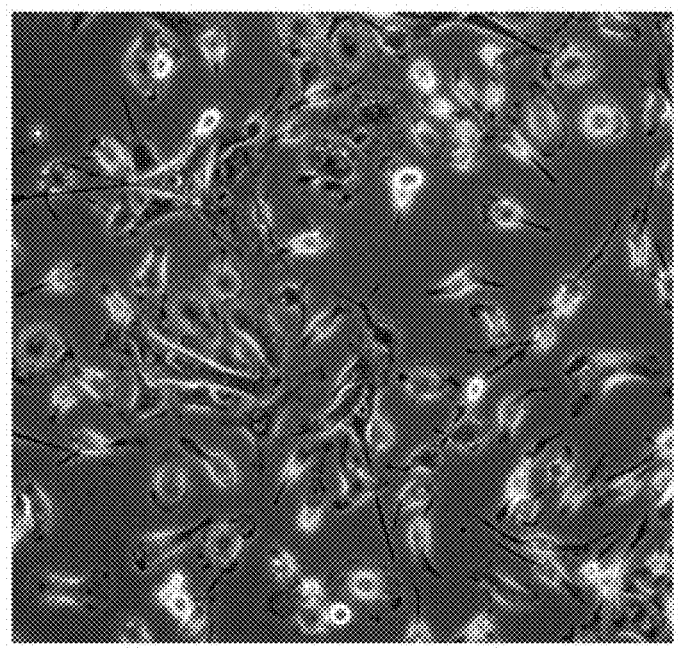
FIG. 11A is an enlarged image with 200× magnification of the first preferred embodiment of the microfluidic device of the present invention, wherein the culture layer has two culture chambers, the fluid layer has one fluid chamber, and the bone marrow cells were cultured in one of the culture chambers.
Figure 11B:
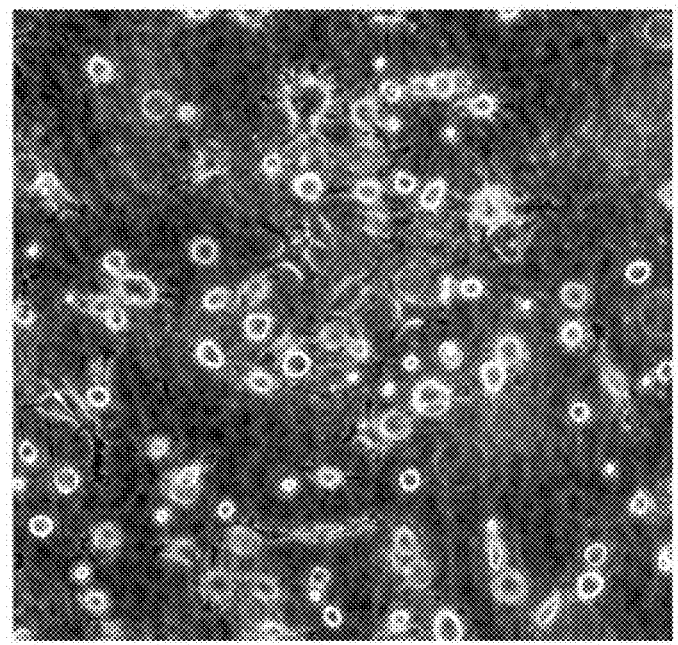
FIG. 11B is an enlarged image with 200× magnification of the first preferred embodiment of the microfluidic device of the present invention, wherein the culture layer has two culture chambers, the fluid layer has one fluid chamber, and the bone marrow cells were 3D cultured in the collagen gel in the other culture chamber.

Four-week-old BALB/c mice were sacrificed, the femurs of the mice were dissected and temporarily soaked in medium at 4° C., and then the mice bone marrow cells (MBM cells) were isolated from mice femurs and cultured in a laminar flow hood (shown as FIG. 11A). After the MBM cells were mixed in a collagen solution, the collagen solution with the MBM cells was poured into one of the culture chambers 123 to form a gel as a 3D cultured group; the other culture chamber 123 of the culture layer 12 was filled with the collagen solution without the MBM cells as a control group. The 3D cultured group and the control group were coated with human umbilical vein endothelial cells (HUVECs) which were pre-stained with red fluorescent (living dye), and the culture layer 12 was incubated in culture medium ready to use, as shown in FIG. 11B.

The microfluidic device was filled with culture medium. The base frame 11, the culture layer 12 with cells, and the flow layer 13 were sequentially assembled into the fluid compartment 10. After the assembled fluid compartment 10 was respectively connected to the peristaltic pump 40 and the aerator 20, which was coated with an antiadhesive by the connecting tube 30 to form a sterile environment and circulatable system for culture medium, the microfluidic device was placed into an incubator for culturing. The HUVECs were confirmed to remain intact by red fluorescent. 10,000 cells of PC3 or LNCaP (Naïve) prostate cancer cells prestained with green fluorescent were added into the fluidic compartment 10 via the aerator 20 after the fluidic compartment 10 was incubated in 5% $CO_2$ incubator for 24 hours. The images of the process of the prostate cancer cells from rolling, adhesion, and crawling on the HUVECs then migrating into the collagen gels, the phase difference, the red fluorescent (HUVECs), and the green fluorescent (prostate cancer cells) were detected by fluorescence microscope or confocal microscope to determine the capability of the microfluidic device of the present invention for assessment of distant metastasis of cancer cells. The PC3 prostate cancer cells obtained from human bone metastatic prostate cancer cells are generally considered as the more aggressive form of metastatic of prostate cancer cell lines, and the LNCaP prostate cancer cells obtained from human metastatic prostate cancer cells are the indolent form. PC3 prostate cancer cells injected into circulation of mice can successfully form bone metastases, while the original LNCaP prostate cancer cells are unable to form distant metastasis.

Figure 13A:
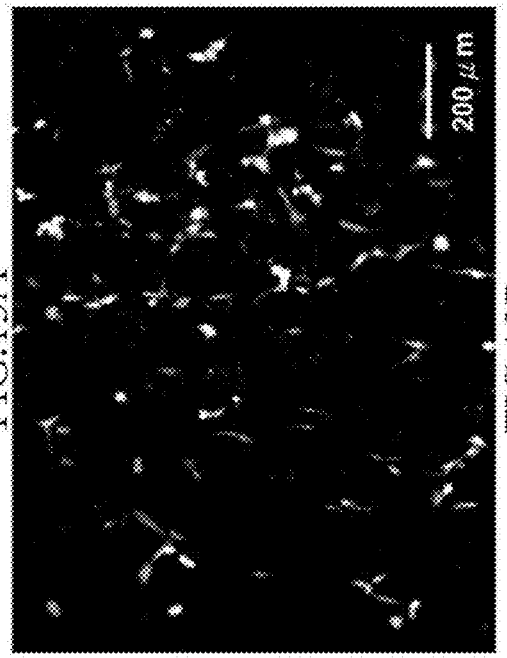
FIG. 13A is an enlarged image with 100× magnification of the 3D cultured group of the first preferred embodiment of the microfluidic device of the present invention, wherein the red florescent displays the human umbilical vein endothelial cells.
Figure 13B:
FIG. 13B is an enlarged image with 100× magnification of the 3D cultured group of the first preferred embodiment of the microfluidic device of the present invention, wherein the green florescent displays the PC3 prostate cancer cells.
Figure 12A:
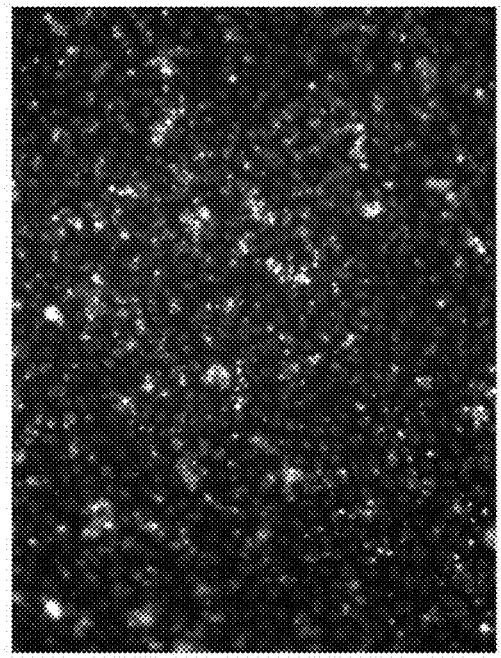
FIG. 12A is an enlarged image with 100× magnification of the control group of the first preferred embodiment of the microfluidic device of the present invention, wherein the red florescent displays the human umbilical vein endothelial cells (HUVECs)
Figure 12B:
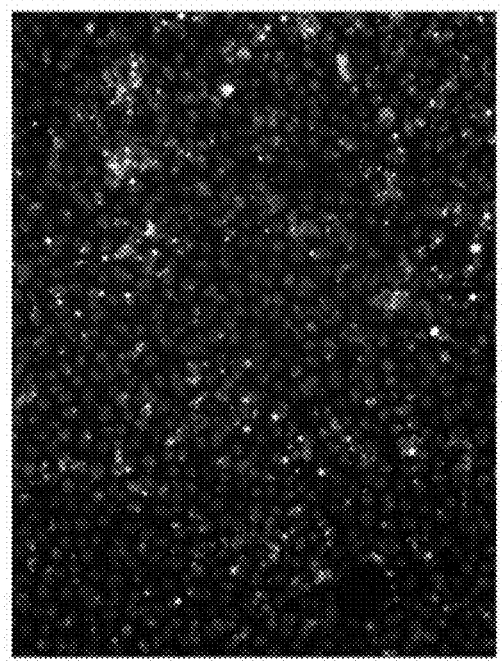
FIG. 12B is an enlarged image with 100× magnification of the control group of the first preferred embodiment of the microfluidic device of the present invention, wherein the green florescent displays the PC3 prostate cancer cells.

As shown in FIGS. 12A and 13A, the HUVECs were respectively observed with red fluorescent imaging to confirm that the HUVECs remained intact after added with the prostate cancer cells for 24 hours. As shown in FIGS. 12B and 13B, according to the prostate cancer cells with green fluorescent, the amounts and appearance of adherent prostate cancer cells of the control group and the 3D cultured group could be observed.

After observation, the cells and the collagen gels were fixed by treating sequentially with PBS and 5% paraformaldehyde for 3 minutes, and then the base layer 121 was taken out from the fluid compartment 10 to perform immunostaining. After immunostaining, the HUVECs and the prostate cancer cells were detected by confocal microscope to ensure whether the prostate cancer cells pass through the HUVECs into the collagen gels.

The results show that the 3D culture formed by culturing the bone marrow cells in collagen solution and then covered with endothelial cells thereon was similar to a microenvironment in bone marrow microvascular tissues (referred to as 3D cultured group). The 3D cultured group successfully attracted more PC3 prostate cancer cells, which were more aggressive (referring to FIG. 13B) compared to the control group with only HUVECs (referring to FIG. 12B). Moreover, the appearance of the PC3 prostate cancer cells of the control group was round while the PC3 prostate cancer cells of the 3D cultured group were of irregular amoeba-like contours, which indicated the PC3 prostate cancer cells of the 3D cultured group were more active. As shown in FIGS. 14A to 14C, the activated PC3 prostate cancer cells of the 3D cultured group were observed by use of confocal microscope, wherein the depth in FIG. 14A was a base line (0 µm), the depth in FIG. 14B was 3 µm below the depth in FIG. 14A (−3 µm), and the depth in FIG. 14C was 8 µm below the depth in FIG. 14A (−8 µm). These results show that most of the activated PC3 prostate cancer cells were under the HUVECs by migration. As shown in FIGS. 15A to 15B (control group) and FIGS. 15C to 15D (3D cultured group), the adherence or activity of LNCaP prostate cancer cells (indolent form) was less than that of PC3 prostate cancer cells at the same experiment.

The above results demonstrate that the fluid compartment 10 of the microfluidic device of the present invention has the following advantages:

1. The present invention can be applied to simulate the organ microenvironment of 3D tissue culture, also allowing the 3D tissue culture preformed in one of the culture chambers without disturbing the control group.

2. The microfluidic device of the present invention can directly observe the fluorescent images clearly by fluorescent microscopy when the cells remain alive and the culture medium circulates without disassembling the microfluidic device.

3. The present invention can simulate the intercellular interaction in tissues and vessels. There is an obvious difference between the 3D cultured group and the control group compared with respect to the appearance and the numbers of adhesive and migrated PC3 prostate cancer cells. Furthermore, the LNCaP prostate cancer cells (indolent form) were less adhesive with less cell migration compared with PC3 prostate cancer cells performed with the same experiment.

4. The base layer 121 of the culture layer 12 of the fluid compartment 10 can be taken out of the fluid compartment 10 after the experiment, and further performed immunostaining and observation.

Example 2 Simulation of Organ Microenvironment for Detecting the Invasion Ability of Cancer Cells from Tissue into Vessel Two different types of cancer cells were respectively immunostained with red or green fluorescent. The two different types of cancer cells then were each mixed in a collagen solution and each filled a respective one of the two culture chambers 123 of the culture layer 12, and then were solidified to form two collagen gels. Finally, the culture layer 12 and the two collagen gels were coated with HUVECs and were incubated in culture medium ready to use.

The microfluidic device was filled with culture medium. The base frame 11, the culture layer 12 with cells, and the flow layer 13 were sequentially assembled into the fluid compartment 10. After the assembled fluid compartment 10 was respectively connected to the peristaltic pump 40 and the aerator 20 without cells by the connecting tube 30 to form a sterile environment of circulation for culture medium, the microfluidic device was placed into an incubator to be cultured for 24 hours. After 24 hours culturing, the cancer cells were collected by medium centrifugation. Calculated amount and the proportion of red fluorescent and green fluorescent cells were used to analyze which type of cancer cells occupies higher proportion, which means higher invasion ability than the other type. Therefore, this result can predict the ability of distant metastasis in different cancer cells.

Example 3 Simulation of Organ Microenvironment for Detecting the Invasion Ability of Cancer Cells from Tissue into Vessel and then to the Other Tissues In this embodiment the microfluidic device had two fluid compartments 10, i.e., the first fluid compartment 10A and the second fluid compartment 10B, and the two fluid compartments are spaced apart and connected by the at least one connecting tube. Each of the culture layers 12A, 12B had two culture chambers 123A, 123B, and each of the fluid layers 132A, 132B had two fluid chambers 1321A, 1321B.

Two different types of cancer cells were respectively immunostained with red or green fluorescent. The two different types of cancer cells were then each mixed with collagen solution and each filled a respective one of the two culture chambers 123A of the culture layer 12A and then solidified to form two collagen gels. Finally, the culture layer 12A and the two collagen gels were coated with HUVECs, and were incubated in culture medium ready to use.

The cells obtained from animal specific organ tissue were mixed with collagen solution and filled one of the culture chambers 123B of the culture layer 12B. The other culture chamber 123B of the culture layer 12B was filled with the collagen solution without the cells as a control group.

The base frame 11A, the culture layer 12A with cells, and the flow layer 13A were sequentially assembled into the first fluid compartment 10A. The base frame 11B, the culture layer 12B with cells, and the flow layer 13B were sequentially assembled into the second fluid compartment 10B. After respectively connecting the first fluid compartment 10A, the second fluid compartment 10B, the peristaltic pump 40, and the aerator 20 by an antiadhesive of the connecting tube 30 (referring to FIG. 16) to form a sterile circulation system for culture medium, the microfluidic device was placed into an incubator and cultured for 24 hours. The cancer cells in the first fluid compartment 10A would move from the collagen gel of the culture layer 12A into the circulation, passed through the connecting tubes 30, and then adhered on the HUVECs of the culture layer 12B of the second fluid compartment 10B. Finally, the cancer cells metastasized into the collagen gel, which contained the cells (simulation of animal tissue metastasis). Therefore, the steps of cancer cell distant metastasis could be simulated in vitro and observed. In the meanwhile, according to the needs, the process of the cancer cells migration through the endothelial cells could be detected by fluorescent microscope or confocal microscope during the experiment. After 48 hours culture, the images of the phase difference, the red fluorescent, and the green fluorescent of the control group and the 3D cultured group of the culture layer 12B of the second fluid compartment 10B were respectively detected by fluorescence microscope to compare the amounts of the adherent cancer cells and their change of appearance.

In the end of the experiment, the cancer cells and collagen gels were fixed by treatment sequentially with PBS and 5% paraformaldehyde for 3 minutes each, and then the culture layers 12A, 12B were taken out from the fluid compartment 10A, 10B to perform immunostaining After immunostaining, the HUVECs and the cancer cells were detected by confocal microscope to ensure whether the cancer cells passed through the HUVECs into the collagen gels.

Even though numerous characteristics and advantages of the present invention have been set forth in the foregoing description, together with details of the structure and features of the invention, the disclosure is illustrative only. Changes may be made in the details, especially in matters of contour, size, and arrangement of parts within the principles of the invention to the full extent indicated by the broad general meaning of the terms in which the appended claims are expressed.

What is claimed is:

1. A microfluidic device, comprising:
(a) at least one fluid compartment, wherein each fluid compartment comprises:
a base frame having a hole defined therein;
a culture layer detachably connected to the base frame, comprising:
a base layer; and
an intermediate layer stacked on the base layer and having at least one opening defined therethrough to form at least one culture chamber; and
a flow layer that is detachably connected to the culture layer so that the culture layer is located between the base frame and the flow layer, and that comprises:
a top frame layer having two opposite ends, having two channels respectively formed on the two opposite ends, and having a hollow provided therethrough between the two channels;
a fluid layer having at least one fluid chamber including two opposite ends disposed on one side of the fluid layer, having an aperture connected to the at least one fluid chamber and disposed on another side of the fluid layer, wherein two grooves are respectively formed on the two opposite ends of the at least one fluid chamber, the two grooves are respectively connected to the two channels of the top frame layer, and the at least one fluid chamber communicates with the at least one culture chamber of the culture layer; and
a transparent layer detachably mounted in the aperture of the fluid layer;
(b) an aerator having an antibacterial cap that is gas permeable and covers a top of the aerator, and having a bottom that is conical;
(c) at least one connecting tube having ends respectively connected to a channel of a top frame layer of a flow layer; and
(d) a peristaltic pump having one end connected to the aerator and having another end connected to the at least one connecting tube so that the peristaltic pump communicates with the at least one fluid compartment.

2. The microfluidic device according to claim 1, wherein each of the two channels of the top frame layer is formed by a bore and a pore communicating with each other, wherein the bores are respectively formed in opposite ends of a surface of the top frame layer which is in contact with the fluid layer, and wherein the pores are respectively formed in opposite sidewalls of the top frame layer.

3. The microfluidic device according to claim 1, wherein the transparent layer of the flow layer has a contour that is larger than that of the at least one fluid chamber of the fluid layer, and the contour of the transparent layer corresponds to that of the aperture of the fluid layer of the flow layer, so that the transparent layer is mounted in the aperture.

4. The microfluidic device according to claim 1, wherein the base frame further comprises multiple magnets which are mounted in the base frame and equidistantly surround the hole of the base frame.

5. The microfluidic device according to claim 4, wherein the multiple magnets are made of neodymium.

6. The microfluidic device according to claim 1, wherein the flow layer further comprises multiple magnets which are mounted in the top frame layer and equidistantly surround the at least one fluid chamber and the hollow of the top frame layer.

7. The microfluidic device according to claim 6, wherein the multiple magnets are made of neodymium.

8. The microfluidic device according to claim 1, wherein the base frame and the flow layer are made of a rigid material.

9. The microfluidic device according to claim 1, wherein the intermediate layer of the culture layer and the fluid layer of the flow layer are made of a material that is plastic and elastic.

10. The microfluidic device according to claim 1, wherein the two channels of the top frame layer have respective inner walls that are further coated with an antiadhesive.

11. The microfluidic device according to claim 1, wherein the aerator has inner walls and the at least one connecting tube is coated with an antiadhesive.

12. The microfluidic device according to claim 1, wherein the base layer of the culture layer and the transparent layer of the flow layer are made of a light permeable material.

13. The microfluidic device according to claim 1, wherein the at least one culture chamber comprises a biocompatible material.

14. The microfluidic device according to claim 1, wherein the base frame, the culture layer, and the flow layer are sandwiched together and tightly connected by multiple magnets, screws, clamps, vacuum suction, or an adhesive.

15. The microfluidic device according to claim 1, wherein the at least one fluid chamber is one fluid chamber and the at least one culture chamber is one culture chamber.

16. The microfluidic device according to claim 1, wherein the at least one fluid chamber is one fluid chamber, and the at least one culture chamber is two culture chambers.

17. The microfluidic device according to claim 1, wherein the at least one fluid compartment is two fluid compartments, and the two fluid compartments are spaced apart and connected by the at least one connecting tube.

18. A method of using the microfluidic device according to claim 1 for cell metastasis, cell invasion or cell adhesion, comprising:
preparing first cells;
culturing the first cells in the at least one culture chamber; and
monitoring the first cells in the at least one culture chamber from the hole of the base frame via the base layer of the culture layer by microscope, or from the hollow of the flow layer via the transparent layer by microscope.

19. The method according to claim 18, wherein preparing first cells further includes mixing the first cells with a biocompatible material.

20. The method according to claim 18, further comprising adding a drug or second cells after culturing the first cells in the at least one culture chamber.

* * * * *